United States Patent [19]

Chavali et al.

[11] Patent Number: 5,683,698

[45] Date of Patent: Nov. 4, 1997

[54] FORMULATION FOR ALLEVIATING SYMPTOMS ASSOCIATED WITH ARTHRITIS

[75] Inventors: Sambasiva R. Chavali, Boston; R. Armour Forse, Brookline, both of Mass.

[73] Assignee: New England Deaconess Hospital, Boston, Mass.

[21] Appl. No.: 691,865

[22] Filed: Aug. 2, 1996

[51] Int. Cl.[6] .................... A61K 35/78; A61K 39/385
[52] U.S. Cl. .................... 424/195.1; 514/825
[58] Field of Search .................... 424/195.1; 514/825

[56] References Cited

U.S. PATENT DOCUMENTS

| | | | |
|---|---|---|---|
| 5,466,452 | 11/1995 | Whittle | 424/195.1 |
| 5,494,668 | 2/1996 | Patwardhan | 424/195.1 |
| 5,529,778 | 6/1996 | Rohatgi | 424/195.1 |

OTHER PUBLICATIONS

Chevallier, A., "The Encyclopedia of Medicinal Plants", DK Publishing, New York, NY. (1996), pp. 58 and 268.

*Primary Examiner*—Marianne M. Cintins
*Assistant Examiner*—M. Moezie
*Attorney, Agent, or Firm*—Hamilton,Brook,Smith & Reynolds, P.C.

[57] ABSTRACT

The invention describes an herbal formulation and its use for reducing/alleviating symptoms associated with rheumatoid arthritis, osteoarthritis and reactive arthritis and for reducing the production of proinflammatory cytokines. Foods and beverages containing the herbal formulation are also described.

22 Claims, No Drawings

FORMULATION FOR ALLEVIATING SYMPTOMS ASSOCIATED WITH ARTHRITIS

BACKGROUND OF THE INVENTION

The manifestation of rheumatoid arthritis (RA) in humans is a consequence of a complex interplay of genetic and environmental factors. The disease is initiated following activation of T cells which is perpetuated when autoantigen reactive T cells and antigen presenting cells are generated. Consequently, autoantibodies (rheumatoid factors) which are directed against host's own immunoglobulins are produced. These processes are further complicated when proinflammatory mediators (such as IL-1, IL-6 and TNF-$\alpha$) are produced in response to signals received from auto reactive T cells. As a result of these factors, the host loses the ability to control immune functions which results in final manifestation of the disease. The important role of TNF-$\alpha$, IL-1$\beta$ and IFN-$\gamma$ in exacerbating the disease process has been demonstrated in several animal models, and many investigators have aimed at regulating the production and synthesis of these proinflammatory mediators to control the disease. Thus, therapeutic approaches are targeted towards modifying the disease process.

Therapy for rheumatoid arthritis is focused around alleviating symptoms associated with the disease, such as relief of pain, reduction of inflammation and increasing range of motion. Aspirin, non-steroidal anti-inflammatory drugs (NSAIDs) (e.g., ibuprofen, naproxen, methotrexate) and glucocorticoids have been used to manage RA. However, these therapeutic agents have a variety of toxic side effects, such as gastric erosion and adverse effects on kidneys and liver, and may inadequately regulate the cellular immune functions and secretions of various cytokines. More recent therapeutic approach include the treatment of patients with multiple drugs has been proven to be more effective. There still remains a need for alternative therapies for the medical management of RA which can eliminate the need for traditional drugs and their associated side effects, particularly over prolonged daily use.

SUMMARY OF THE INVENTION

This invention describes a formulation and use of the formulation to reduce and alleviate symptoms associated with arthritis, such as rheumatoid arthritis, osteoarthritis and reactive arthritis. The formulation can also reduce the production of proinflammatory cytokines such as tumor necrosis factor, IL-1 and IL-6. The formulation comprises an herbal extract from the roots, rhizomes and/or vegetation of six herbal plant varieties. In particular, the herbs are a combination of species of Alpinia, Smilax, Tinospora, Tribulus, Withania and Zingiber. A preferred formulation comprises *Alpinia galanga*, *Smilax glabra*, *Tinospora cordifolia*, *Tribulus terrestris*, *Withania somnifera* and *Zingiber officinale*, each present in a physiologically acceptable amount.

The herbal formulation can itself be administered, in a therapeutically effective amount, to an individual to alleviate symptoms associated with arthritis, or it can be used as an ingredient in foods and beverages which are designed for daily consumption as part of a therapeutic regimen for arthritis, or as a prophylatic regimen for individuals having a genetic predisposition to arthritis. Suitable foods and beverages in which the herbal formulation can be incorporated within, without special processing requirements, include but are not limited to, nutritional beverages, soft drinks, fruit beverages, baked goods, dips and spreads, salad dressings, puddings, condiments, confections, snack foods, ice cream, frozen confections and novelties, margarine-like spreads, seasonings such as for meat, poultry, seafood and salads, and non-baked, extruded foods such as bars.

Daily ingestion of the formulation of this invention can replace or supplement traditional drug therapies and provides the patient suffering from arthritic symptoms with relief from joint stiffness, inflammation and improved joint range of motion. The incorporation of the formulation into daily foods/beverages enables the patient to adhere to a daily therapeutic regimen in an unobtrusive manner and provides immediate therapeutic benefit.

DETAILED DESCRIPTION OF THE INVENTION

This invention is based upon the discovery of an herbal formulation that, when administered as part of a routine therapeutic regimen to individuals diagnosed with rheumatoid arthritis, has the ability to reduce/alleviate the physical symptoms associated with arthritis. The formulation of this invention comprises aqueous extracts from the roots, rhizomes and/or vegetation of the following herbs: Alpinia species, especially *Alpinia galanga* and *Alpinia officinarum*; Smilax species, especially *Smilax glabra*, *Smilax sarsaparilla* and *Smilax china*; Tinospora species, especially *Tinospora cordifolia*; Tribulus species, especially *Tribulus terrestris*; Withania species, especially *Withania sominifera*; and Zingiber species, especially *Zingiber officinale*.

The formulation of this invention is prepared by the aqueous extraction of roots, rhizomes and/or vegetation from the six varieties of herbs described herein. A detailed description of the extraction process and the preferred portion of the plant are provided in the Exemplification section. The term "extract" as used herein is intended to mean a concentrate of aqueous soluble plant components from the portion of the plant extracted and can be in aqueous or powdered form. After the extract from each herb is obtained (either liquid or powder form), they are admixed together in amounts that are physiologically acceptable to the patient. There are no special means for mixing required. The mixture of herbal extracts can be encapsulated, tableted or formulated with a physiologically acceptable vehicle into unit dosages.

A unit dosage can comprise a therapeutically effective amount of each herbal extract for a single daily administration (e.g., orally or by feeding tube in an enteral diet); or it can be formulated into smaller quantities of each ingredient to provide for multiple doses in a day. In either instance, the formulation of this invention can be manufactured into tablets, capsules, caplets, elixirs, enteral formulations or incorporated into slow-releasing carriers. Examples of physiologically acceptable vehicles include water, oil emulsions, alcohol or any of the food/beverage formulations described herein.

A unit dosage, as stated above, will depend upon many factors including age, condition and disease state of the patient and the number of times the unit will be taken in a single day. In any event, the entire daily dosage will be that which is physiologically acceptable to an individual and can be administered daily over a prolonged period of time. Physiologically acceptable amounts of each herb are as follows:

*Alpinia galanga*: from about 100 mg/kg/day to about 500 mg/kg/day;

*Smilax glabra*: from about 50 to about 100 mg/kg/day;

*Tinospora cordifolia*: maximum of about 16 mg/kg/day;
*Tribulus terrestres*: from about 50 to about 100 mg/kg/day;
*Withania sominifera*: maximum of about 100 mg/kg/day;
*Zingiber officinale*: maximum of about 2.5 mg/kg/day.

A preferred unit dosage of each herbal extract will be from about 2 to about 5 mg/kg/day. Thus, the total amount from all of the extracts will be from about 10 to about 30 mg/kg/day. This is well below the tolerance limit.

Alternatively, the formulation can be incorporated within or used on many of the foods and beverages one can consume on a daily basis. Suitable foods and beverages which could be made, include but are not limited to, nutritional beverages, soft drinks, fruit beverages and juices, electrolyte containing beverages, puddings, baked goods (i.e., cookies, brownies, fudge, cake, breads), non-baked extruded foods (i.e., bars), salad dressings, condiments, confections (i.e., candy), snack foods (i.e., chips, pretzels, tortillas), dips and spreads, ice cream, frozen confections and novelties, margarine-like spreads, seasonings such as for meat, poultry, seafood and salads. Fat free, reduced fat and low calorie versions of these foods are embraced by this invention. Incorporation of the herbal formulation into foods/beverages provides the advantages of patient compliance over a prolonged period of use and in a form which is more desirable to the consumer, rather than in the form of a medicament.

The herbal formulations may be coformulated with dietary fats enriched with mono-unsaturated fatty acids, such as oleic acid, (e.g., sesame seed oil, olive oil, canola oil), linoleic acid (e.g., safflower oil) or with α-linolenic acid and γ-linolenic acid (e.g., black current seed oil, borage oil). Examples of suitable foods include margarine-like spreads, oil-in-water emulsions, salad dressings, and the like.

A study was conducted on RA patients to determine the efficacy of the herbal formulation. The primary criteria in evaluating the efficacy was the degree of relief of pain and swelling and how the patients felt after taking the medication. After an eight week study of patients taking the herbal formulation orally, four times per day, patients reported improved range of motion in their joints and decreased swelling in one or multiple joints of the elbows, knees, ankles and hands. Chronic pain caused by the joint swelling had also been reduced.

Not only were physical changes observed in the patient group taking the formulation but there were positive chemical changes observed in the patients undergoing daily ingestion of this formulation. In general, a significant decrease in the elevated levels of proinflammatory cytokines (TNF-α, IL-1β and IL-6) was considered indicative of a positive therapeutic effect. Proinflammatory cytokines (IL-β, TNF and IL-6) were measured in whole blood drawn from patients in the study at 0 and 8 weeks on the program. A significant decrease in these indicators was observed. These data coupled with physical improvement indicated that the herbal formulation was effective for alleviating symptoms of arthritis and can reduce the production of proinflammatory cytokines.

The herbal formulation contains ingredients derived from six herbs which influence various immune functions, such as curtailing inflammatory responses, improving cellular functions (e.g., decrease production of IL-1, TNF, IL-6 and reducing T and B cell functions) and curtailing the production of proinflammatory cytokines. With these immunological changes, a patient with arthritis is expected to physically improve in terms of pain and joint swelling within days on an oral or enteral therapeutic regimen. Reduction of pain and swelling and increased range of joint motion are expected over prolonged daily use of the formulation.

Other physical advantages are also possible with a daily ingestion of the formulation of this invention, such as resistance to common infections which typically trigger symptoms of arthritis. Erythrocyte sedimentation rate (ESR), an indicator of susceptibility to infection, was conducted on the rheumatoid arthritis patients who participated the study at 0 and 8 weeks. A significant decrease in ESR compared to basal levels was observed in patients taking the herbal formulation over the course of the study, thus indicating that the patients were less susceptible to infection, such as bacterial, viral or parasitic infections.

The benefit of down-regulating the production of proinflammatory medicators has importance for individuals other than those who have arthritis. For example, the formulation could be administered as a therapeutic or prophylactic for individuals who suffer from allergies and/or inflammation. For instance, it has been shown by the clinical study described herein that proinflammatory cytokines are down regulated and that B cells and T cells function can be down regulated. Other autoimmune diseases that are T-lymphocyte mediated can be similarly treated with the herbal formulation of this invention. Examples of other diseases include Crohn's disease, ulcerative colitis, systemic lupus erythematosus.

Although the focus of the invention discussed above is for human therapy, it is also contemplated to use the herbal formulation of this invention as a therapeutic or prophylatic for non-human mammals, including domestic and farm animals, having arthritis or other T cell mediated immune disease for which it is desirable to reduce/suppress immune response or alleviate joint pain and stiffness caused by these diseases. The skilled artisan would readily ascertain the mode and method of therapy based upon the animal to be treated. For example, the herbal formulation can be incorporated into the animal's water source or feed, or it can be administered like a medicament in the form of a capsule, tablet, liquid or the like.

The invention will now be further illustrated by the following non-limiting exemplification:

EXEMPLIFICATION

Formulation Preparation

The roots (Smilax, Tribulus, Withania), rhizomes (Alpinia, Zingiber) and/or whole plant (Tinospora) were crushed into pieces, then soaked in water maintained at 60° C. for overnight. The decoction was filtered, and concentrated using a custom made (industrial) roto-vapor using a 10 liter flask. The resultant paste was dried at 60° C. in an oven for overnight to obtain dry powder. This procedure was followed for all the extracts. The different dry powder extracts were mixed using a mixer, and the extracts were filled into gelatin capsules (0-size) using a capsule filling machine, as follows: 100 mg *Alpinia galanga*; 100 mg *Smilax glabra*; 100 mg *Tinospora cordifolia*; 100 mg *Tribulus terrestris*; 50 mg *Withania sominifera*; and 50 mg *Zingiber officinale*.

Patient Study

A panel of patients were interviewed and screened for physical symptoms of rheumatoid arthritis (RA). The patients were ranked on a scale of 1 to 8 for severity of their symptoms associated with RA. The criteria for the ranking included chronic pain and swelling in the joints of elbows, knees, ankles and hands. Patients experiencing pain and/or swelling in one joint were considered to have an score of 1, and the maximum score for patients who complained of pain and swelling in all the joints was 8. The results are summarized in the Table at the end of this section.

The patients were then tested for RA factor using the latex agglutination test described by Singer, J. M. and C. M. Plotz, Am. J. Med. 27:888–896 (1956) and Hansen et al., Am. J. Clin. Pathol. 73:110–113 (1980). Erythrocyte sedimentation rate (ESR) levels were also tested to determine whether a patient was resistant to infection. Only those patients who tested positive for RA factor were selected for the study.

All selected patients were required to refrain from taking any medication for three days immediately prior to the study, including NSAIDs. The patients were given a four-week supply of the herbal formulation and were asked to consume at least four capsules per day. The patients were asked to return for a clinical evaluation at 4 and 8 weeks after recruitment in the study. At week 4, patients were given a second four-week supply of the herbal formulation. Every patient was asked subjective questions about the pain and swelling in each joint, and the information was recorded. Any untoward side effects were also recorded. Based on the information obtained following subjective questioning, the RA score was calculated and the mean ± standard error is shown in the Table. The RA factor testing and the ESR determinations were repeated on each patient at week 8.

Cytokines

The effects of consuming the formulation on the productions of various cytokines and interleukins was investigated to understand their effects on cellular functions based on the productions of various mediators. A significant decrease in the elevated levels of proinflammatory cytokines (TNF-α, IL-1β, IL-6) and IL-10 was expected if the formulation exerted any significant therapeutic effect. An elevation in the levels of IL-10 which possess anti-inflammatory properties of down-regulating the levels of TNF-α, IL-1β, IL-6 may be beneficial to RA patients. On the other hand, IL-10 could activate T cells leading to T-cell hypersensitivity. The production of IL-10 in response to both LPS (which accounts for IL-10 of non-T cell source; i.e., B cells and macrophages) was determined to understand functions of various cells and their response to the individual herbal components of the formulations.

On each patient visit, the venous blood samples were collected (between 9 and 11 am) from the patients and approximately 2 ml aliquots were transferred into 12×75 mm vaccutainer tubes containing sodium EDTA. Lipopolysaccharide (LPS) from E. coli 055:B5 (Difco Labs, Detroit, Mich.) (1 ng/ml final concentration) was used as a stimulus for macrophages and B cells. Saline (0.9% w/v) (control) or LPS (0.05% v/v) were introduced in the tubes under sterile conditions using a tuberculin syringe. To prevent the blood from settling, the tubes were then placed on a varimix tilter (maintained at 30° angle, and tilting 100 times/hour) which was kept in a 37° C. incubator. Plasma samples were separated at 0 hours (spontaneous), 8 hours or 24 hours after the initiation of incubation. The samples were stored at −20° C. until the study was completed and then shipped on dry ice to a laboratory for analyses of cytokines using appropriate enzyme linked immunosorbent assay (ELISA) kits (Biosource International, Camarillo, Calif.) and used according to manufacturer's specifications (human TNFα: catalog no. KHC 3013; human IL-10: catalog no. KHC 0103; IL-6: catalog no. KHC 0063; IL-1β: catalog no. 0012).

Results

Consumption of the herbal formulation significantly decreased the proinflammatory mediators, ESR levels and provided relief of RA pains and swellings. The results are reported in the Table.

TABLE

| Rx. | TNF-α (pg/ml) | IL-1β (pg/ml) | IL-6 (ng/ml) | IL-10 (pg/ml) | ESR (mm/h) | RA score |
|---|---|---|---|---|---|---|
| B-0 | 111 ± 10 | 7.8 ± 0.42 | 10.2 ± 0.66 | 17.00 ± 1.63 | 55.5 ± 8.1 | 6.5 ± 1.3 |
| T-8 | 126 ± 11 | 5.2 ± 0.53* | 7.8 ± 0.75* | 14.5 ± 1.49* | 26.5 ± 3.5* | 3.0 ± 1.2 |

(*)indicates level of significance ($P < 0.05$) compared to the basal levels as determined by matched paired t-test.
Data represents mean ± standard error.
n = 33 patients

Equivalents

Those skilled in the art will recognize, or be able to ascertain, using no more than routine experimentation many equivalents to the specific embodiments of the invention described herein. Such equivalents are intended to be encompassed by the following claims:

We claim:

1. A formulation comprising an extract from roots, rhizomes and/or vegetation of:
   a) Alpinia;
   b) Smilax;
   c) Tinospora;
   d) Tribulus;
   e) Withania; and
   f) Zingiber,
   each present in a physiologically acceptable amount.

2. The formulation of claim 1 further comprising a physiologically acceptable vehicle.

3. The formulation of claim 1 wherein the formulation is a powder, capsule, tablet, liquid, caplet or enteral formulation.

4. The formulation of claim 1 further comprising a dietary fat selected from the group consisting of oleic acid, linoleic acid, α-linolenic acid, γ-linolenic acid and combinations thereof.

5. A formulation comprising an extract from roots, rhizomes and/or vegetation of:
   a) *Alpinia galanga;*
   b) *Smilax glabra;*
   c) *Tinospora cordifolia;*
   d) *Tribulus terrestris;*
   e) *Withania somnifera;* and
   f) *Zingiber officinale,* each present in a physiologically acceptable amount.

6. The formulation of claim 5 further comprising a physiologically acceptable vehicle.

7. The formulation of claim 5 wherein the formulation is a powder, capsule, tablet, liquid, caplet or enteral formulation.

8. The formulation of claim 5 further comprising a dietary fat selected from the group consisting of oleic acid, linoleic acid, α-linolenic acid, γ-linolenic acid and combinations thereof.

9. A food or beverage comprising the formulation of claim 1.

10. A food or beverage comprising the formulation of claim 5.

11. A method for reducing the production of proinflammatory cytokines in a mammal, comprising administering a therapeutically effective amount of the formulation of claim 1.

12. The method of claim 11 wherein the formulation is administered orally or by feeding tube in an enteral diet.

13. The method of claim 11 wherein the mammal is a human.

14. A method for reducing the production of proinflammatory cytokines in a mammal, comprising administering a therapeutically effective amount of the formulation of claim 5.

15. The method of claim 14 wherein the formulation is administered orally or by feeding tube in an enteral diet.

16. The method of claim 14 wherein the mammal is a human.

17. A method for alleviating symptoms associated with rheumatoid arthritis comprising administering a therapeutically effective amount of the formulation of claim 1 to an individual.

18. The method of claim 17 wherein the formulation is administered orally or by feeding tube in an enteral diet.

19. A method for alleviating symptoms associated with rheumatoid arthritis comprising administering a therapeutically effective amount of the formulation of claim 5 to an individual.

20. The method of claim 19 wherein the formulation is administered orally or by feeding tube in an enteral diet.

21. A method for reducing the erythrocyte sedimentation rate in an individual, comprising administering a therapeutically effective amount of the formulation of claim 1.

22. A method for reducing the erythrocyte sedimentation rate in an individual, comprising administering a therapeutically effective amount of the formulation of claim 5.

* * * * *